(12) United States Patent
Galdonik et al.

(10) Patent No.: US 7,988,705 B2
(45) Date of Patent: Aug. 2, 2011

(54) STEERABLE DEVICE HAVING A COREWIRE WITHIN A TUBE AND COMBINATION WITH A FUNCTIONAL MEDICAL COMPONENT

(75) Inventors: Jason A. Galdonik, Hanover, MN (US); James Pokorney, Northfield, MN (US); Matthew F. Ogle, Oronoco, MN (US)

(73) Assignee: Lumen Biomedical, Inc., Maple Grove, MN (US)

( * ) Notice: Subject to any disclaimer, the term of this patent is extended or adjusted under 35 U.S.C. 154(b) by 1330 days.

(21) Appl. No.: 10/979,439

(22) Filed: Nov. 2, 2004

(65) Prior Publication Data

US 2005/0209631 A1 Sep. 22, 2005

Related U.S. Application Data

(60) Provisional application No. 60/550,880, filed on Mar. 6, 2004.

(51) Int. Cl.
*A61M 29/00* (2006.01)

(52) U.S. Cl. ........... 606/200; 604/104; 604/101.02; 604/103.01; 604/103.12; 604/509; 604/510; 606/113; 606/213; 606/151; 606/159; 606/191; 606/194; 606/198; 600/31

(58) Field of Classification Search .......... 604/104, 604/101.02, 103.01, 103.12, 34, 509, 510; 606/113, 200, 213, 151, 159, 191, 198, 194; 600/31

See application file for complete search history.

(56) References Cited

U.S. PATENT DOCUMENTS

| 4,610,662 A | 9/1986 | Weikl et al. |
| 4,723,549 A | 2/1988 | Wholey et al. |
| 4,728,319 A | 3/1988 | Masch |
| 4,784,636 A | 11/1988 | Rydell |
| 4,790,812 A | 12/1988 | Hawkins, Jr. et al. |
| 4,794,928 A | 1/1989 | Kletschka |
| 4,873,978 A | 10/1989 | Ginsburg |
| 4,883,460 A | 11/1989 | Zanetti |
| 4,887,613 A | 12/1989 | Farr et al. |

(Continued)

FOREIGN PATENT DOCUMENTS

EP 0117940 A2 12/1984

(Continued)

OTHER PUBLICATIONS

Feldman, "Transcatheter Aspiration of a Thrombus in an Aortocoronary Saphenous Vein Graft," Am. J. Cardiol. Aug. 1, 1987, 60(4), 379-380.

(Continued)

*Primary Examiner* — Nicholas D Lucchesi
*Assistant Examiner* — Scott Medway
(74) *Attorney, Agent, or Firm* — Dardi & Herbert, PLLC; Peter S. Dardi; Mengmeng Fahrni

(57) ABSTRACT

An integrated guiding device has a tube and a corewire within the tube and a torque coupler. The torque coupler can couple the rotational motion of the tube with the rotational motion of the corewire. The wire can be moved longitudinally at least some amount relative to the tube. The device can further comprise a functional medical structure, such as an embolism protection structure. The device can be used in medical procedures, such as less invasive procedures within the cardiovascular system. Improved fiber based embolism protection devices comprise fiber bundles that are twisted prior to delivery.

20 Claims, 9 Drawing Sheets

U.S. PATENT DOCUMENTS

| | | | |
|---|---|---|---|
| 4,994,067 A | 2/1991 | Summers | |
| 5,011,488 A | 4/1991 | Ginsburg | |
| 5,011,490 A | 4/1991 | Fischell et al. | |
| 5,053,008 A | 10/1991 | Bajaj | |
| 5,059,178 A | 10/1991 | Ya | |
| 5,102,415 A | 4/1992 | Guenther et al. | |
| 5,108,419 A | 4/1992 | Reger et al. | |
| 5,125,906 A * | 6/1992 | Fleck | 604/171 |
| 5,152,277 A | 10/1992 | Honda et al. | |
| 5,163,906 A | 11/1992 | Ahmadi | |
| 5,188,621 A | 2/1993 | Samson | |
| 5,211,651 A | 5/1993 | Reger et al. | |
| 5,404,888 A * | 4/1995 | Kontos et al. | 600/585 |
| 5,501,694 A * | 3/1996 | Ressemann et al. | 606/159 |
| 5,546,958 A | 8/1996 | Thorud et al. | |
| 5,549,626 A | 8/1996 | Miller et al. | |
| 5,571,122 A * | 11/1996 | Kelly et al. | 606/159 |
| 5,599,307 A | 2/1997 | Bacher et al. | |
| 5,720,764 A | 2/1998 | Naderlinger | |
| 5,766,191 A | 6/1998 | Trerotola | |
| 5,810,874 A | 9/1998 | Lefebvre | |
| 5,814,064 A | 9/1998 | Daniel et al. | |
| 5,836,868 A | 11/1998 | Ressemann et al. | |
| 5,843,051 A | 12/1998 | Adams et al. | |
| 5,897,567 A | 4/1999 | Ressemann et al. | |
| 5,911,725 A | 6/1999 | Boury | |
| 5,911,734 A | 6/1999 | Tsugita et al. | |
| 5,928,260 A | 7/1999 | Chin et al. | |
| 5,935,139 A | 8/1999 | Bates | |
| 5,938,645 A | 8/1999 | Gordon | |
| 5,941,869 A | 8/1999 | Patterson et al. | |
| 5,972,019 A | 10/1999 | Engelson et al. | |
| 5,997,557 A | 12/1999 | Barbut et al. | |
| 6,010,522 A | 1/2000 | Barbut et al. | |
| 6,022,336 A | 2/2000 | Zadno-Azizi | |
| 6,066,149 A | 5/2000 | Samson et al. | |
| 6,135,991 A | 10/2000 | Muni et al. | |
| 6,142,987 A | 11/2000 | Tsugita | |
| 6,146,396 A | 11/2000 | Konya et al. | |
| 6,159,195 A | 12/2000 | Ha et al. | |
| 6,168,579 B1 | 1/2001 | Tsugita | |
| 6,203,561 B1 | 3/2001 | Ramee et al. | |
| 6,206,868 B1 | 3/2001 | Parodi | |
| 6,238,412 B1 | 5/2001 | Dubrul et al. | |
| 6,258,115 B1 | 7/2001 | Dubrul | |
| 6,270,477 B1 | 8/2001 | Bagaoison et al. | |
| 6,277,139 B1 * | 8/2001 | Levinson et al. | 606/200 |
| 6,346,116 B1 * | 2/2002 | Brooks et al. | 606/200 |
| 6,361,545 B1 | 3/2002 | Macoviak et al. | |
| 6,368,338 B1 * | 4/2002 | Konya et al. | 606/200 |
| 6,391,044 B1 * | 5/2002 | Yadav et al. | 606/200 |
| 6,454,741 B1 | 9/2002 | Muni et al. | |
| 6,454,775 B1 * | 9/2002 | Demarais et al. | 606/128 |
| 6,485,500 B1 | 11/2002 | Kokish | |
| 6,514,273 B1 | 2/2003 | Voss et al. | |
| 6,558,405 B1 | 5/2003 | McInnes | |
| 6,569,148 B2 | 5/2003 | Bagaoisan et al. | |
| 6,596,011 B2 | 7/2003 | Johnson et al. | |
| 6,610,077 B1 | 8/2003 | Hancock et al. | |
| 6,620,148 B1 | 9/2003 | Tsugita | |
| 6,695,865 B2 * | 2/2004 | Boyle et al. | 606/200 |
| 6,702,834 B1 * | 3/2004 | Boylan et al. | 606/200 |
| 6,805,692 B2 | 10/2004 | Muni et al. | |
| 6,911,036 B2 | 6/2005 | Douk et al. | |
| 7,052,500 B2 | 5/2006 | Bashiri et al. | |
| 7,056,328 B2 * | 6/2006 | Arnott | 606/200 |
| 7,229,463 B2 * | 6/2007 | Sutton et al. | 606/200 |
| 2001/0044632 A1 * | 11/2001 | Daniel et al. | 606/200 |
| 2002/0035347 A1 | 3/2002 | Bagaoisan | |
| 2002/0062133 A1 | 5/2002 | Gilson et al. | |
| 2002/0095174 A1 * | 7/2002 | Tsugita et al. | 606/200 |
| 2002/0111648 A1 | 8/2002 | Kusleika et al. | |
| 2002/0143362 A1 * | 10/2002 | Macoviak et al. | 606/200 |
| 2002/0151927 A1 * | 10/2002 | Douk et al. | 606/200 |
| 2002/0169472 A1 | 11/2002 | Douk et al. | |
| 2002/0183782 A1 * | 12/2002 | Tsugita et al. | 606/200 |
| 2003/0023263 A1 | 1/2003 | Krolik et al. | |
| 2003/0135232 A1 | 7/2003 | Douk et al. | |
| 2004/0006365 A1 | 1/2004 | Brady et al. | |
| 2004/0153118 A1 | 8/2004 | Clubb et al. | |
| 2005/0021075 A1 | 1/2005 | Bonnette et al. | |
| 2005/0085847 A1 | 4/2005 | Galdonik et al. | |
| 2006/0030876 A1 | 2/2006 | Peacock, III et al. | |
| 2008/0109088 A1 | 5/2008 | Galdonik et al. | |

FOREIGN PATENT DOCUMENTS

| | | |
|---|---|---|
| EP | 1226795 A2 | 7/2002 |
| GB | 2020557 A | 11/1979 |
| WO | WO 95/05209 | 2/1995 |
| WO | WO 98/38930 | 9/1998 |
| WO | 0016705 A1 | 3/2000 |
| WO | WO 02/055146 | 7/2002 |
| WO | WO 02/085092 | 10/2002 |

OTHER PUBLICATIONS

Nakagawa et al., "A Retrievable Nitinol Vena Cava Filter: Experimental and Initial Clinical Results," J. of Vascular and Interventional radiology, May-Jun. 1994; 5:507-512.

4DG Fibers: http://web.archive.org/web/2011030070010/http://fitfibers.com/4DG_Fibers.htm; (Oct. 30, 2001).

Fiber Innovative Technology: biocomponent and specialty fibers; FIT Capabilities; http://web.archive.org/web/20010217040848/http://www.fitfibers.com/capablities.htm (Feb. 17, 2001).

Fiber Innovative Technology: biocomponent and specialty fibers; FIT Capabilities; http://web.archive.org/web/20010408003529/http://www.fitfibers.com/product.htm, (Apr. 8, 2001).

* cited by examiner

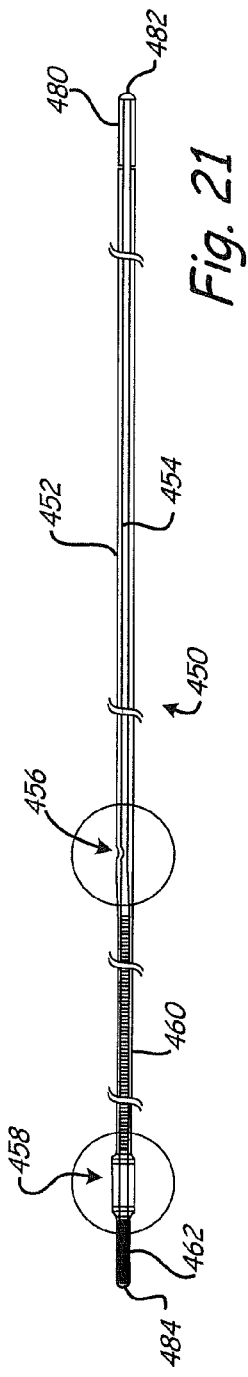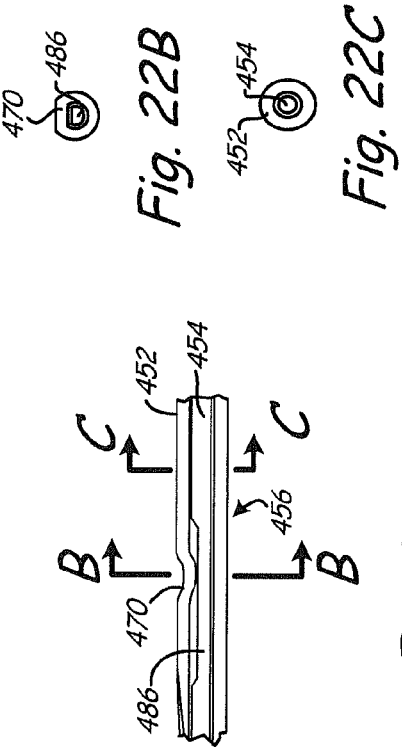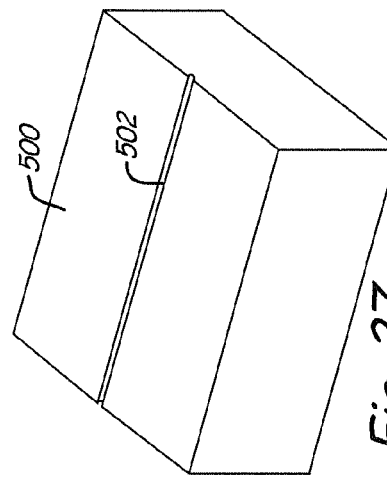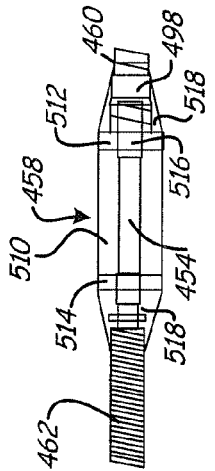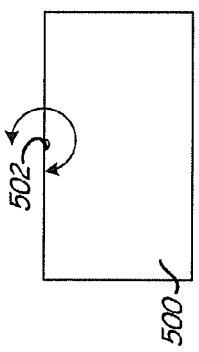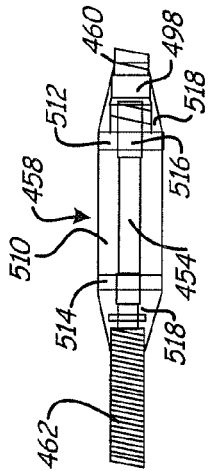

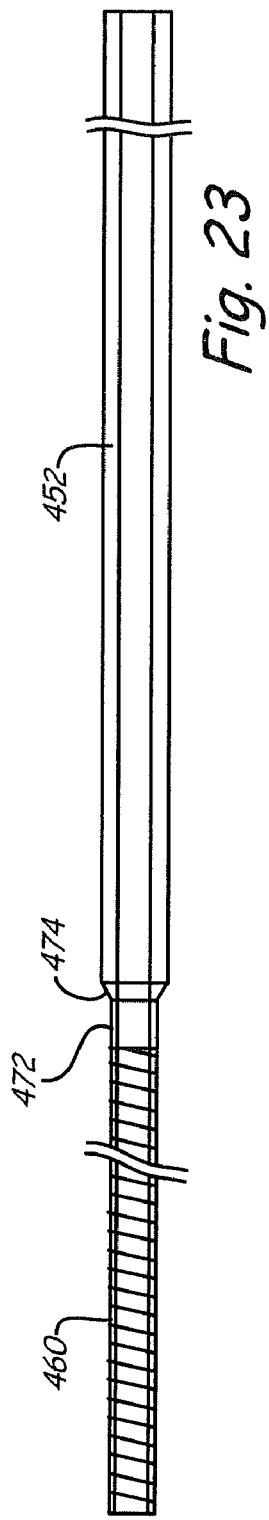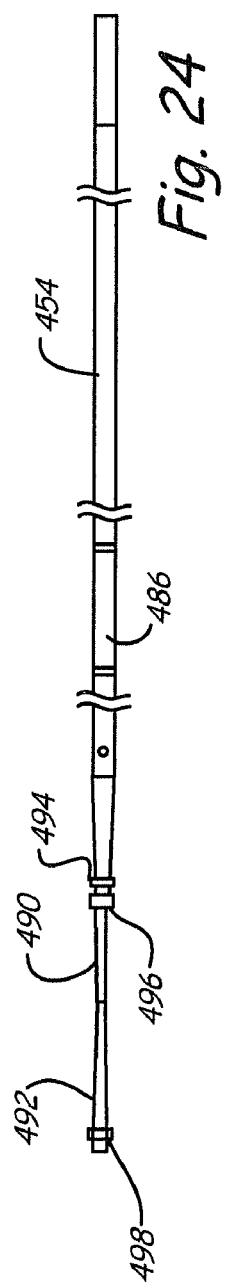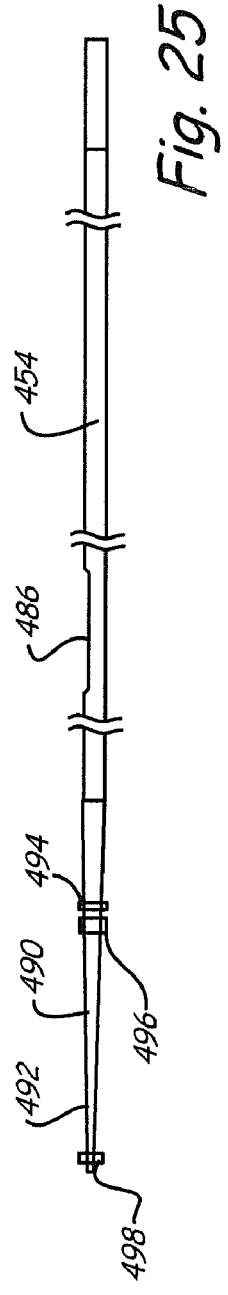

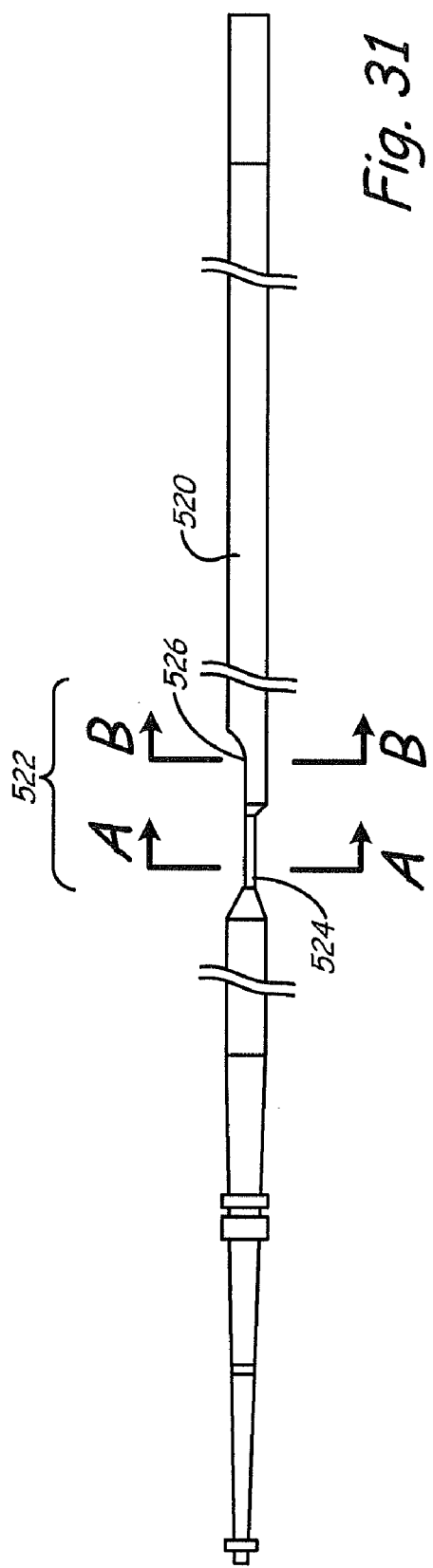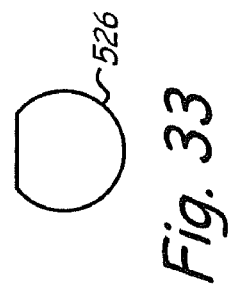
Fig. 31
Fig. 33
Fig. 32

STEERABLE DEVICE HAVING A COREWIRE WITHIN A TUBE AND COMBINATION WITH A FUNCTIONAL MEDICAL COMPONENT

CROSS REFERENCE TO RELATED APPLICATIONS

This application claims priority to copending provisional patent application Ser. No. 60/550,880 to Picorney et al. filed on Mar. 6, 2004, entitled "Steerable Guide Wire and Shaft With Small Diameters," incorporated herein by reference.

FIELD OF THE INVENTION

The invention relates to guiding devices for less invasive medical procedures and guide devices combined with additional functional medical components, such as actuatable medical structures, such as embolism protection structures. The invention further relates to procedures for using steerable guide devices alone and with functional medical components such as embolism protection structure. In addition, the invention relates to improved designs for embolism protection devices based on fibers.

BACKGROUND OF THE INVENTION

A variety of procedures are performed with less invasive approaches to reach distant locations within a patient's body. These procedures can be used, for example, for entry into the abdominal cavity or into the urinary track, or for reaching the patient's genitals. However, many of the procedures are performed within the cardiovascular system. For any of these procedures, a guidewire can be used to snake through the patient to position the tip of the guidewire at a desired location. A catheter and/or other medical devices can be positioned by sliding them over the guidewire to the appropriate location.

Generally, to position the guidewire, the guidewire traverses along a pathway, such as through vessels of the cardiovascular system, that has bends and branches. To navigate along the curves and branches, the guidewire and catheters are flexible. However, to steer the device to the desired location, some control generally should be possible with respect to directing the tip of the device for steering the device along curves and branches in the desired pathway. In particular, to guide the tip of the device, it is desirable to be able to apply torque to the end of the guidewire from the proximal end of the device under the control of the physician or other health care professional. Through the application of torque, the tip can be guided along a selected path within the patient.

Many less invasive procedures create the possibility of emboli formation as a result of the procedure. Also, some procedures may be specifically initiated to capture and/or remove emboli, which are generated or have a risk of being generated through another mechanism. An embolus can be any particle comprising a foreign and/or native material, which enters the vascular system or other vessel of the body with potential to cause occlusion of flow, e.g., blood flow. Emboli can be formed from aggregates of fibrin, blood cells or fragments thereof, collagen, cholesterol, plaque, fat, calcified plaque, bubbles, arterial tissue, and/or other miscellaneous fragments or combinations thereof Emboli can lodge, for example, in the narrowing regions of medium size blood vessels that feed the major organs. Loss of blood flow to surrounding tissue causes localized cell death or microinfarcts. Cerebral microinfarcts can cause stroke leading to confusion, disturbance of speech, paralysis, visual disturbances, balance disturbances and even death. In the heart, emboli can cause myocardial infarcts, i.e. heart attacks. Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding microinfarctions/microinfarcs. Resulting impairments are frequently short term but can be permanent.

Many clinical procedures can result in emboli including, for example, coronary, carotid, and peripheral interventions. In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause microinfarcts and/or myocardial infarctions and left ventricular dysfunction.

A significant reason for ischemic injury during percutaneous procedures can be generation of emboli that block smaller distal vessels. One approach to curb this complication has been to use pharmacological therapies during the time of the intervention. Limited therapeutic success has been reported with the use of calcium channel blockers, adenosine, and sodium nitroprusside (Webb, J G, Carere, R G, Virmani, R, Baim, D, Teirstein, P S, Whitlow, P, McQueen, C, Kolodgie, F D, Buller, E, Dodek, A, Mancini, G B, & Oesterle, S: Retrieval and analysis of particulate debris after saphenous vein graft intervention. *J Am Coll Cardiol* 2000, 34:468-475, incorporation herein by reference.). Glyoprotein IIb/IIIa inhibitors have been used for percutaneous coronary interventions to reduce platelet aggregation, but also fail to show meaningful long term clinical benefit. (Mathew, V, Grill, D E, Scott, C G, Grantham, J A, Ting, H H, Garratt, K N, & Holmes, D R, Jr. The influence of abciximab use on clinical outcome after aortocoronary vein graft interventions. *J Am Coll Cardiol* 1999, 34:1163-1169 and Mak, K H, Challapalli, R, Eisenberg, M J, Anderson, K M, Califf, R M, & Topol, E J: Effect of platelet glycoprotein IIb/IIIa receptor inhibition on distal embolization during percutaneous revascularization of aortocoronary saphenous vein grafts. EPIC Investigators. Evaluation of IIb/IIIa platelet receptor antagonist 7E3 in Preventing Ischemic Complications. *Am J Cardiol* 1997, 80:985-988, both of which are incorporated herein by reference.) Since embolization often develops from physical disruption of fibrotic plaque, a mechanism of therapeutic embolic protection specifically targeted at prevention of platelet aggregation and blood clotting may have little effect on these already-formed, embolizable plaques.

SUMMARY OF THE INVENTION

In a first aspect, the invention pertains to a biocompatible integrated guiding device comprising a tube with an internal lumen, a corewire within the lumen of the tube, and a torque coupler. The torque coupler can couple the rotational motion of the tube with the rotational motion of the corewire. The corewire can be moved longitudinally at least some amount within the lumen of the tube. The device can further comprise a functional medical structure, such as an embolism protection structure.

In another aspect, the invention pertains to a method for selectively placing a corewire within a patient by inserting a biocompatible integrated guiding device into the patient through an incision. The corewire is then directed to a desired location within the patient. The placement can involve rotation of a tube to direct the distal tip of a corewire within the tube by way of a torque coupler. The method can further relate to the deployment of a functional medical device such as an embolism protection structure.

In a further aspect, the invention pertains to a method for guiding a medical device having a wire within the lumen of a tube and a torque coupler that rotationally couple the tube and the wire. The method comprises engaging an element of the torque coupler associated with the wire with an element of the torque coupler associated with the tube.

In other aspects, the invention pertains to an embolism protection device comprising a corewire and a bundle of fibers fastened together at a first end that is free to move relative to the corewire and fastened collectively to the corewire at a second end. The bundle of fibers have a configuration with the fibers being generally aligned. Also, the respective ends of the fiber bundle are twisted relative to each other about an axis aligned along the corewire.

BRIEF DESCRIPTION OF THE DRAWINGS

FIG. 21 is a sectional side view of a specific embodiment of an integrated guiding device.

FIG. 22A is a fragmentary, expanded sectional side view of the torque coupler of the device of FIG. 21.

FIG. 22B is a sectional view of the torque coupler of FIG. 22A taken along line B-B.

FIG. 22C is a sectional view of the device of FIG. 22A taken along line C-C.

FIG. 23 is a sectional side view of the tube of the integrated guiding device of FIG. 21.

FIG. 24 is a top view of the corewire of the device of FIG. 21 separate from the tube.

FIG. 25 is a side view of the corewire of the device of FIG. 21 separate from the tube with the side view being 90 degrees rotated from the top view in FIG. 24.

FIG. 27 is a perspective view of a fixture block.

FIG. 28 is an end view of the fixture block of FIG. 27.

FIG. 29 is a fragmentary expanded end view of the channel within the fixture block of FIG. 27.

FIG. 30 is a fragmentary side view on an embolism protection structure of the integrated guiding device of FIG. 21.

FIG. 31 is a side view of an alternative embodiment of the corewire.

FIG. 32 is a sectional view of the corewire of FIG. 31 taken along line A-A of FIG. 31.

FIG. 33 is a sectional view of the corewire of FIG. 31 taken along line B-B of FIG. 31.

DETAILED DESCRIPTION OF THE INVENTION

Figure 1:
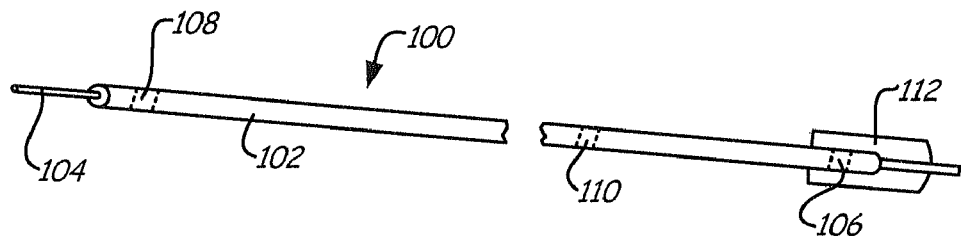
FIG. 1 is a perspective view of a tube with a corewire extending within the central lumen of the tube.

An integrated guiding device comprises a thin corewire and a small diameter tubing/catheter, e.g., a hypotube or polytube, that goes over the corewire with a torque coupler to couple the small diameter tubing to the corewire. The torque coupler provides considerable advantages with respect to delivery of the integrated guiding device while providing for desired longitudinal relative motion of the corewire and tube. The integrated guiding device can be used for the delivery of appropriate medical treatment devices and the like. In addition, the integrated guiding device can comprise the tube and corewire along with a functional medical component, such as an actuatable medical strucuture or the like, integrated into the integrated guiding device structure, as described further below for an embolism protection structure, which filters fluid flow to entrap emboli. The functional medical structure, for example, can be located near the distal end of the corewire. In particular, the longitudinal movement of the corewire with respect to the small tube provides for actuating features of a functional medical component coupled with the integrated guiding device, while the torque coupling provides excellent steerability for delivery of the devices. In some embodiments, for convenience the tube has the outer dimensions approximating a standard guidewire. If the tube has the outer dimensions of a standard guidewire, interventional devices such as balloons, stents and the like can be delivered over tube as with a standard guidewire or hypotube. Additional flexibility results from the ability to provide distant communication from the distal end to the proximal end through the relative longitudinal motion of the corewire and the tube.

The integrated guiding device generally comprises a thin corewire, a tube over the corewire and a torque coupling structure that couples torque on the tube with torque on the corewire, such as near or at the distal end of the corewire. In some embodiments of interest, by parsing the diameter of a standard guidewire into a thinner corewire and a small diameter tubing or tube, structure is introduced that can communicate between the proximal end and the distal end by longitudinally moving the corewire and the hypotube relative to each other. Thus, the integrated guiding device has a structure that can take advantage of these features with respect to manipulations at the distal end from the proximal end. At the same time, the outer surface of the tube can be used as a guide to introduce additional treatment devices that can be delivered over standard guidewires. However, to be effective, the corewire of the integrated guiding device should be positionable within the patient. To achieve this objective, generally torque has to be applicable to the distal end of the integrated device through the application of torque at the proximal end external to the patient such that the corewire can be manipulated by the physician/health care professional to guide the corewire to a specific location within the body. The integrated guiding device can be sufficiently flexible to follow branches of a patient's vascular system. The integrated guiding device facilitates guidance of the corewire and promotes design flexibility of the integrated device.

While in some embodiments the corewire and tube have especially thin cross sections, in other embodiments the corewire can have conventional thicknesses of a guidewire and the tube can have conventional dimensions of a catheter. However, for embodiments in which the corewire and tube have particularly thin cross sections, due to the extremely thin nature of the corewire, the wire can twist such that torque cannot be efficiently transferred from the distal end of the corewire to the proximal end of the corewire without the presence of the torque coupler. For any of the embodiments, to facilitate transfer of torque from the distal end to the proximal end, the corewire and tube can be coupled together to provide to torque transmittal, i.e., rotational communication, from the tube to the corewire.

The integrated guiding device generally comprises a torque coupling structure that couples torque on the tube with torque on the corewire. Due to the thicker profile of the tube, the corewire rotationally coupled to the tube can more effectively transmit torque from the proximal end of the device to the distal end of the corewire. Thus, a torque coupling structure is generally located near the distal end of the tube and the corewire. However, the torque coupling structure can extend along the entire length of the tube or any reasonable fraction thereof. With this structure, torque applied to the proximal end of the tube and/or corewire can result in efficient transfer of torque on the distal end of the corewire. In some embodiments, the integrated guiding device comprises one or more additional torque coupling structures, for example, near the proximal end of the tube and corewire and/or at or neat the center of the tube.

Suitable torque couplers can provide rotational coupling between the tube and the corewire. In some embodiments, the torque coupling is always present, while in other embodiments the torque coupling is only present when the torque coupler is actuated. If the torque coupler is not always engaged, longitudinal motion between the tube and the corewire may or may not be possible when the torque coupler is engaged. In general, longitudinal motion between the tube and the corewire is possible at selected times. Thus, for embodiments in which the torque coupler is always engaged, longitudinal motion between the tube and the corewire is generally always available unless some other functional feature prevents the longitudinal motion at particular times.

Various structures can be used to provide the desired rotational coupling. For example, the tube can provide a key way that engages the corewire as a key. In other words, the corewire has structure that engages corresponding structure on the tube. This lack of circular symmetry of the corewire and inner surface of the tube provide the desired rotational coupling. This rotational engagement of the corewire and tube can be only over a portion of the length of the corewire, generally at least a portion of which is toward the distal end of the tube. Such a key way-key structure can provide the rotational coupling without preventing relative longitudinal motion of the corewire and tube, although the longitudinal motion may be restricted over a particular range. Specifically, by limiting the longitudinal extent of the torque coupler, the longitudinal motion of the corewire relative to the tube may be limited and/or the torque coupling may be limited to specific longitudinal alignments of the corewire and the tube. Several specific embodiments are described below.

In alternative embodiments, the rotational motion itself alters the structure to engage the rotational coupling. For example, in one embodiment below, a coil associated with the tube engages the corewire upon the application of rotational motion such that the tube becomes rotationally coupled to the corewire. Also, in other embodiments, threads on the tube and corewire can be engaged to rotationally couple the tube and the corewire. In additional embodiments, the rotational coupling may only be provided at select times. For example, a compressible section of the tube can be compressed to provide the desired rotational coupling at a selected time. Also, an electromagnetic coupling can be engaged at selected time to provide rotational coupling of the tube and the corewire. If the rotational coupling is engaged at select times, longitudinal motion may be restricted during these limited times while allowing relative longitudinal motion of the tube and corewire when the rotational coupling is not engaged.

While an integrated guiding device as described herein can be conveniently used for the delivery of additional medical devices over the tube, one or more functional medical structures can be incorporated into the integrated guiding device. In particular, it can be desirable to interface the functional medical structures with both the corewire and the tube. By interfacing the functional medical structure to the corewire and the tube, the longitudinal motion of the corewire with respect to the tube can be used to send a signal to the functional medical structure from outside of the patient's body. Specifically, the longitudinal motion of the corewire and the tube can be used to actuate or de-actuate the functional medical structure. Suitable functional medical structures include, for example, embolism protection components.

In general, desirable embolism protection structures can be formed using filtering media with a three dimensional filtering matrix such as provided by a bundle of fibers. A fiber-based embolism protection component connected to an integrated guiding device is described further below. In this device, the fibers are attached at one end to the corewire and at the other end to the tube, e.g., a hypotube. The device can be deployed with the fibers stretched into a relatively low profile configuration. Upon longitudinal pulling the corewire proximal relative to the tube, the fibers flare outward to a deployed configuration in which the device can provide filtering within a patient's vessel. Reversal of the longitudinal motion of the corewire relative to the tube can stretch the fibers to a removal configuration. Additional embodiments of embolism protection devices are described in copending U.S. patent application Ser. No. 10/414,909 to Ogle, entitled "Embolism Protection Device," incorporated herein by reference. Aspiration can be applied during the removal of the device, as described further in copending U.S. patent application Ser. No. 10/854,920 filed May 27, 2004 to Galdonik et al., entitled "Emboli Filter Export System," incorporated herein by reference.

Specifically, the materials and structure of the device can be selected to have porosity that would allow blood elements, such as white blood cells (about 7-20 microns), red blood cells (8-9 microns) and platelets (2-4 microns), yet collects emboli. In contrast, emboli generally range in size with diameters from about 20 microns to about 3.5 mm, in some embodiments from about 45 microns to about 1000 microns and in further embodiments from about 50 microns to 200 microns. A person of ordinary skill in the art will recognize that additional ranges of emboli within the explicit ranges are contemplated and are within the present disclosure. Thus, in some embodiments of interest, the trapping of emboli with a size larger than about 45 microns to about 50 microns would be beneficial.

In general, the desired filtering properties and corresponding average pore sizes and pore size distributions of an embolism protection device may depend on the particular location of the particular vessel in which it is delivered. However, for many applications it can be desirable to block the flow of a substantial majority of particulates with a diameter of at least about 0.2 mm while allowing the flow of a substantial majority of particulates with a diameter of no more than about 0.001 mm, and in other embodiments, to block the flow of a substantial majority of particulates with a diameter of at least about 0.1 mm while allowing the flow of a substantial majority of particulates with a diameter of no more than about 0.01 mm. A person of ordinary skill in the art will recognize that additional ranges of filtering ability within the explicit ranges are contemplated and are within the present disclosure. A substantial majority of particulates can be considered to be at least about 99 percent.

In some embodiments, the fiber-based embolism protection device comprises surface capillary fibers. Experiments indicate that devices formed with surface capillary fibers provide excellent filtering properties. Embolism protection devices with surface capillary fibers are described further in copending U.S. patent application Ser. No. 10/795,131 filed Mar. 6, 2004 to Galdonik et al., entitled "Fiber Based Embolism Protection Device," incorporated herein by reference. It has been discovered that the twisting of a fiber bundle, such as an SCF fiber bundle, in an embolism protection device can assist with keeping the fibers free of gaps during deployment and can result more consistent performance of the filter following deployment in a patient. Rotationally locking the tube to the corewire allow for the fiber bundle to be twisted and for the twist to be preserved through sterilization and final use of the device. In some embodiments, gentle heat can be added during the manufacturing process to impart a shape memory into the polymer, although heat is not required for consistent performance of the device or for elimination of gaps in the deployed fibers. In further additional or alternative embodiments, the fiber bundle can be twisted while the fibers are being deployed. This twisting during deployment within the patient results in even more consistent fiber placement within the deployed device.

The integrated guiding devices described herein can be used effectively to guide the corewire and associated medical devices through intricate pathways within the body. Specifically, devices can be guided into coronary arteries as well as along similar highly branched and curved pathways. The maneuverability has been confirmed for embodiments described below using animal studies and human model systems. The improved maneuverability has been confirmed in comparison with commercial systems that are available. Thus, the integrated guiding devices described herein can provide improved performance for a range of medical procedures involving less invasive intervention.

In summary, the integrated guiding devices described herein provide for very small diameter components with excellent maneuverability while maintaining desirable degrees of freedom. The integrated guiding devices used with integral medical structures and/or with associated medical devices delivered over the tube can be positioned precisely within the body with less effort while providing desired functionality by the ability to longitudinally move the corewire and the tube relative to each other. Thus, functionality can be maintained without sacrificing the ease of steering of the device to a selected location within a patient's body.

General Structure of the Integrated Guiding Device

In general, an integral guiding device comprises a corewire, a tube over the corewire, a torque coupler, and one or more optional, functional medical structures connected to the corewire and/or tube. The torque coupler provides coupling of rotational motion between the corewire and the tube, which may or may not be maintained at all times. An integrated guiding device, as described herein, is shown schematically in FIG. 1. Device 100 comprises tube 102, corewire 104, first torque coupler 106, second torque coupler 108, third torque coupler 110 and functional medical structure 112. The length of tube 102, e.g., a hypotube or a polytube, can generally be selected for the particular application. For example, for intervention in the aorta, the tube generally would have a length from about 190 cm (63 inches) to about 300 cm (106 inches). The cross section of the tube can be characterized by an inner diameter and an outer diameter. The inner diameter general ranges from about 0.001 inches to about 0.01 inches, in further embodiment from about 0.003 inches to about 0.008 inches and in additional embodiments from about 0.005 inches to about 0.007 inches. The outer diameter generally ranges from about 0.04 inches to about 0.009 inches, in further embodiments from about 0.03 inches to about 0.010 inches, in additional embodiments from about 0.02 inches to about 0.011 inches and in other embodiments from about 0.015 inches to about 0.013 inches, with standard guidewire outer diameters being about 0.014 inches. The corewire has a diameter just slightly less than the inner diameter of the tube by about 0.002 inches to about 0.003 inches. A person of ordinary skill in the art will recognize that additional ranges within the explicit ranges for the diameters are contemplated and are within the present disclosure.

In some embodiments, the corewire has a length such that the corewire extends past the distal end of the tube while extending also from the proximal end of the tube. Generally, the corewire extends from the proximal end of the tube to provide for independent manipulation of the corewire relative to the tube, especially for longitudinal movement and from the distal end for attachment to a medical device such as grippers or an embolism protection device. The proximal end of the corewire can have a gripper or the like that both facilitates gripping the proximal end of the corewire and simplifies longitudinal movement. The distal end can have one or more coils over the corewire to provide flexibility and Radio-opacity while maintaining overall diameter.

In general, the tube 102 and corewire 104 can be formed from one or more of various materials, such as polymers, metals and combinations thereof. The tube and corewire may or may not be formed from the same material. Suitable materials are generally biocompatible in that they are non-toxic, non-carcinogenic and blood compatible and do not induce hemolysis or a significant immunological response. Suitable biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy.

Suitable polymers include, for example, synthetic polymers as well as purified biological polymers and combinations thereof Suitable synthetic polymers include, for example, polyamides (e.g., nylon), polyesters (e.g., polyethylene teraphthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

In other embodiments, the surface of the corewire, the inner surface of the tube, the outer surface of the tube, portions thereof or combinations thereof is coated with a friction reducing agent. Suitable friction reducing agents include, for example, suitable polymers, such as polytetrafluorethylene, i.e., Teflon® or a coating such as parylene. The coating of the corewire can facilitate relative longitudinal motion of the corewire relative to the tube.

The outside of tube 102 or corewire 104 or a portion thereof, such as a portion at or near the distal end, can have surface capillary fibers associated with the surface. The attachment of the surface capillary fibers generally depends on the material of the surface. For example, covalent bonding and/or adhesives can be used for the attachment. Surface capillary fibers have contoured surfaces with one or more surface capillaries along the length of the fiber or a portion thereof. The surface capillary fibers can moderate the character of fluid flow along the surface, such as reducing turbulence and can be used to effectively deliver bioactive agents in a controlled fashion. The use of surface capillary fibers in medical devices generally and catheters and associated articles is described further in copending U.S. patent application Ser. No. 10/781,503 to Ogle et al., filed on Feb. 18, 2004, entitled "Medical Article Incorporating Surface Capillary Fiber," incorporated herein by reference.

Torque couplers 106, 108, 110 generally provide at least temporary torque coupling without preventing at appropriate times relative longitudinal motion of the tube and the corewire. Various designs can accomplish this objective. In some embodiments, due to the very thin nature of the corewire, torque applied at the proximal end can fade as a result of twisting of the wire such that the amount of rotation at the distal end is less than desired relative to the rotation at the proximal end. The tube is also thin, and also may transfer torque poorly. However, by coupling the rotational motions of both members, the rotation of the distal end of the corewire can be controlled more precisely in the coupled system by rotating the tube at the proximal end. The torque coupler(s) couples the rotational motions of the two components.

In particular, the torque couplers can provide at least temporary angular engagement of the tube with the corewire. This engagement can be constrained to localized regions such as a region at or near the distal end of the tube, a region at or near the proximal end of the tube and/or a region between the locations at or near the respective ends of the tube. In particular, it can be desirable to have rotational coupling between the tube and the corewire within twenty centimeters of the distal end of the wire and in some embodiments within about four centimeters from the distal end of the tube. Generally, it is advantageous to couple the tube and corewire in a distal-most region if the desired goal is efficient transfer of torque to the distal tip. In some embodiments the rotational coupling extends along the entire length of the tube.

Several specific embodiments are depicted in the Figures. In some embodiments, tube 102 and corewire 104 comprise a key way with a matched key that engage each other to rotationally restrict the movement of corewire 104 within tube 102. In these embodiments, the corewire does not have a circular cross section, at least not along its entire length. A variety of different structures are possible for the key way/key combinations with three embodiments shown in FIGS. 2, 3 and 5.

Figure 2:
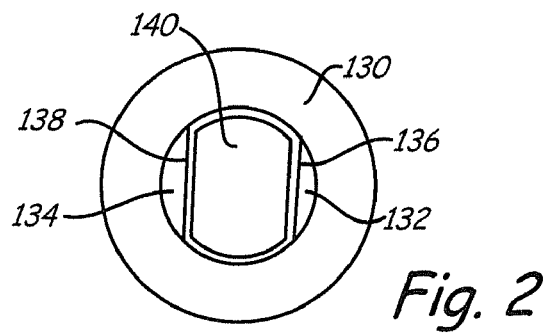
FIG. 2 is a sectional view of a first embodiment of a torque coupler with a key way-key structure rotationally connecting the tube and corewire of FIG. 1.
Figure 3:
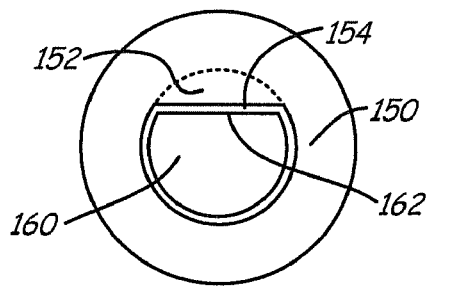
FIG. 3 is a sectional view of an alternative embodiment of a torque coupler with a key way-key structure rotationally connecting the tube and corewire of FIG. 1.

Referring to FIG. 2, a tube 130 has two key ways portions 132, 134 along the inner diameter that break the circular symmetry of the inner diameter and forms an asymmetric key way that engages the asymmetrical corewire as the key. In particular, key way portions 132, 134, respectively, have flat surfaces 136, 138 that engage corewire 140. Corewire 140 has a cross section that corresponds with the interior of tube 130. Specifically, corewire 140 has flat surfaces 142, 144 that engage flat surfaces 136, 138, respectively. An alternative embodiment is shown in FIG. 3. As depicted in FIG. 3, tube 150 has one key way portion 152 forming an engaging surface 154. Corewire 160 fits within the inner lumen of tube 150. Corewire 160 has a corresponding engaging surface 162 that breaks the circular symmetry of the cross section of the corewire and that allows the corewire to function as a key. Engaging surface 162 engages surface 154 of tube 150. Other embodiments are similarly possible, for example with three of more key way portions projecting into the inner lumen of the tube, in addition, to the one and two key way portion embodiments of FIGS. 2 and 3. Also, the shape of the engaging surface does not need to be flat as long as the engaging surfaces of the tube and the corewire rotationally couple the tube and the corewire.

Figure 4:
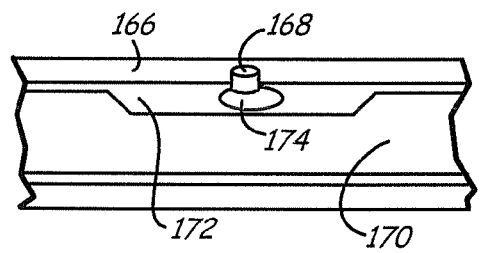
FIG. 4 is fragmentary, sectional side view of tube and corewire with a port opening into the tube adjacent a key in the corewire that forms a mold for forming a key way associated with the tube.

The phantom lines in FIGS. 2 and 3 indicate that the key ways may or may not be formed from the same material as the remaining portions of the tube. The key ways of the tube can be integrally formed into the tube or formed within the tube, for example, with a polymer such as an epoxy. For example, to form the key ways of FIGS. 2 and 3, an adhesive or polymer can be injected into the lumen of the tube through a port or the like. The port can be formed by laser cutting or other suitable drilling process. Upon curing, the adhesive/polymer forms the key way. The corewire can be coated with a non-stick coating, such as polytetrafluoroethylene (Teflon®) or parylene. Referring to FIG. 4, tube 166 has a port 168. Wire 170 has a key 172 that forms a mold for the adhesive/polymer 174.

Figure 5:
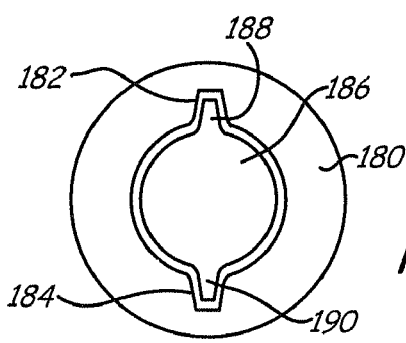
FIG. 5 is a sectional view of a second alternative embodiment of a torque coupler with a key way-key structure rotationally connecting the tube and corewire of FIG. 1.

As shown in FIGS. 2 and 3, the tube key way extends into the interior lumen of the tube. In additional embodiments, the tube key way more resembles a recess or indentation, and one or more projecting key elements from the corewire extends into the key way. As shown in FIG. 5, an embodiment has a tube 180 with notches 182, 184 that act as key ways for engaging corewire 186. Corewire 186 has two ridges or teeth 188, 190 that fit within notches 182, 184. The shape, size and other features of notches 182, 184 and ridges 188, 190 can be selected based on particular design considerations by a person of ordinary skill with the constraint that the ridges fit within the notches. Similarly, the number of notches and ridges can be one, two, three, four or more as appropriate. The notches and ridges can be formed along with the respective tube and corewire, for example, by extrusion, or they can be formed subsequently, for example, by machining, molding or adhering the appropriate structures.

The projecting key ways of FIGS. 2 and 3 can be combined with notch key ways of FIG. 5 in a single embodiment if desired. Similarly, the distinction may be blurred in some embodiments whether or not the key way is a projection into the lumen or a notch from the lumen into the tube structure. The significant feature is that a key way and key are mated such that the tube rotationally engages the corewire.

As shown in FIGS. 2, 3 and 5, the tube and corewire rotationally engage each other with a key way-key relationship that does not inhibit relative longitudinal motion of the tube and corewire along the length of the elements. This relationship is based on the assumption that the key way extends along the entire length of the tube. Thus, torque can be transmitted from the tube to the corewire without interfering with the capability to move longitudinally the tube relative to the corewire. However, the longitudinal dimension of the key way and/or the corresponding key structure of the corewire generally can be along the entire length of the tube and/or the corewire or only a portion of the length. For example, the key way and key can be limited to a location at or near the distal, at or near the proximal end and/or at one or more locations more central to the tube or corewire structures.

Depending on the design of the key and key way, limiting the key way to only a portion of the length of the device can have various effects. In some embodiments, this localization can result in the torque coupling at only corresponding longitudinal positions of the corewire and tube with free rotation at other locations. In other embodiments, a notch in the tube can be localized within a key way on the corewire to limit the longitudinal motion of the corewire relative to the tube. A specific embodiment with this configuration is described in detail below. A variation of this embodiment with restricted longitudinal motion is described below with torque coupling in some longitudinal relationships and rotational freedom in other longitudinal relationships. For the deployment of a fiber-based embolism protection device, it can be desirable to rotate the fiber bundle while deploying the fibers from a low profile configuration to a configuration with the fibers extending across the vessel lumen. The amount of rotation generally is at least about 15 degrees, in further embodiments from about 45 degrees to about 450 degrees and in other embodiments from about 90 degrees to about 405 degrees. A person of ordinary skill in the art will recognize that additional ranges of rotation are contemplated and are within the present disclosure.

If the key way/key structures do not extend along the entire length, the projecting structure, whether the key way or the key, generally extends for a shorter longitudinal length such that the interference of the key with the tube away from the key way does not undesirably interfere with the longitudinal degree of movement of the corewire relative to the tube. If the key way does not extend along the entire length of the tube, the relative longitudinal motion of the tube relative to the corewire may be limited. In particular, the projecting structure generally can only traverse within the extent of the corresponding indented structure. However, some limitation on the longitudinal motion may be desirable since in operation only a limited amount of longitudinal motion can provide the desired functionality while providing additional control of the limits of the movement.

If the key way and key extend along the entire length of the tube and corewire, the corewire can be inserted within the tube after they are formed. However, if the key way and key only extend over a portion of the length of the components, generally some of the structure is formed following insertion of the corewire into the tube. An example of this is described in more detail below.

Figure 6:
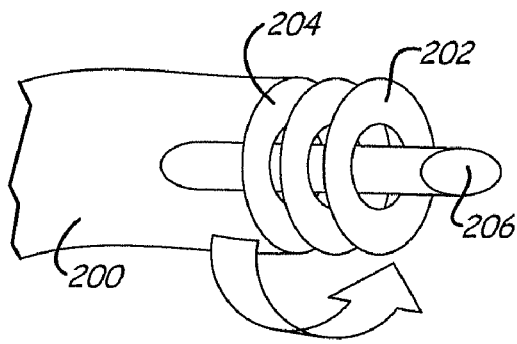
FIG. 6 is a schematic, fragmentary perspective view of a torque coupler with a coil at the end of the tube of FIG. 1 for rotational coupling with the corewire.
Figure 7:
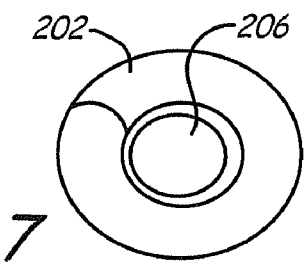
FIG. 7 is a sectional view of the torque coupler of FIG. 6 depicting the coil surrounding the corewire wherein they are disengaged.
Figure 8:
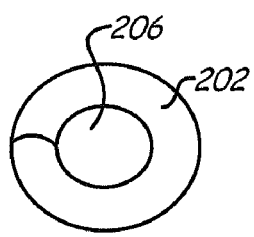
FIG. 8 is a sectional view of the torque coupler of FIG. 6 depicting the coil engaged with the corewire.

Another embodiment of a torque coupler is shown schematically in FIG. 6. As shown in FIG. 6, tube 200 has a coil 202 located at its distal end 204. Coil 202 extends over corewire 206. In its relaxed state, corewire 206 can move freely within coil 202, as shown in FIG. 7. However, upon rotation in the appropriate direction, coil 202 can tighten onto corewire 206 such that motion of the tube is coupled to corewire 206, as shown in FIG. 8. Thus, torque can be applied to the distal end of corewire 206 by applying torque to tube 200. Coil 202 can be formed from appropriate spring metals or other material. A person of ordinary skill in the art can select the dimensions and elasticity of the coil to yield desired degrees of coupling between the coil and the corewire. Using this embodiment, temporary coupling can be provided to rotationally couple the tube and the corewire while providing for relative longitudinal motion of the tube and corewire at other times.

Figure 9:
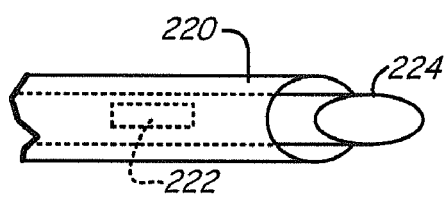
FIG. 9 is a schematic, fragmentary perspective view of a torque coupled based on a compression section.

In a further embodiment, tube 220 has a compressible section 222, as shown in FIG. 9. Corewire 224 extends within the internal lumen of tube 220. Compressible section 222 generally has an elasticity such that compressible section 222 can be pressed with a reasonable force against corewire 224 to couple tube 220 to corewire 224. Compressible section 222 can be formed, for example, by machining away a section of tube 220 and adding a plug of an appropriate material, such as an elastomeric polymer. An appropriate seal can be formed to prevent leakage of liquid at the compressible section. Thus, tube 220 and corewire 224 can be selectively coupled to provide for rotational coupling when desired and uncoupled when desired to allow for relative longitudinal motion. Compressible section 222 can be placed near the proximal end of the tube such that the compressible section can be engaged by a health care professional, such as a physician, during a procedure using the tube and corewire. In some embodiments, the compressible section is engaged by hand by pressing on the compressible section. This torque coupling element with a compressible section can be combined with other torque coupling elements, such as a torque coupling element at or near the distal end of the tube, for example, the types of torque coupling elements described above.

Figure 10:
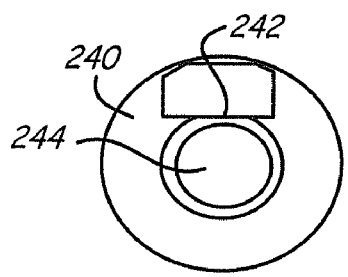
FIG. 10 is a sectional view of a torque coupler based on threads along the inside of the tube and threads on the outside of the corewire in which the threads are not engaged.
Figure 11:
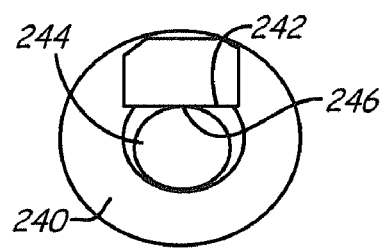
FIG. 11 is a sectional view of the torque coupler of FIG. 10 in which the threads are engaged.

In a further embodiment, the inner surface of the tube and the outer surface of the corewire have threads at a location along the length of the components. Rotation of the tube relative to the corewire can engage the threads and rotationally couple the tube to the corewire, while disengagement of the threads can allow for relative longitudinal movement of the tube and the corewire. Referring to FIG. 10, the cross section of a tube 240 with threads 242 is depicted with a threaded corewire 244 within the inner lumen of tube 240 with the threads disengaged. Referring to FIG. 11, threads 244 are shown engaging threads 246 of corewire 244. Threads 242 and 246 can be formed, for example, using standard approaches in the art. The threaded sections can be located at or near the distal end of the tube and corresponding portion of the corewire, although the threaded section or additional threaded sections can be placed at other locations along the length of the tube and corewire. While the presence of threads my limit the longitudinal movement of the tube and the corewire, for example, restricting motion in one direction, this may be adequate for many applications.

Figure 12:
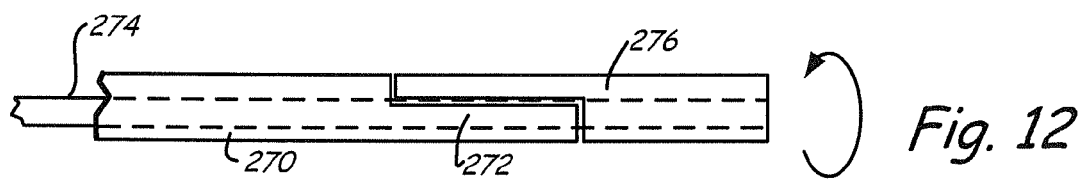
FIG. 12 is a side view of an alternative embodiment of a torque coupler with elements of the torque coupler attached, respectively, at the end of the tube and the corewire.
Figure 13:
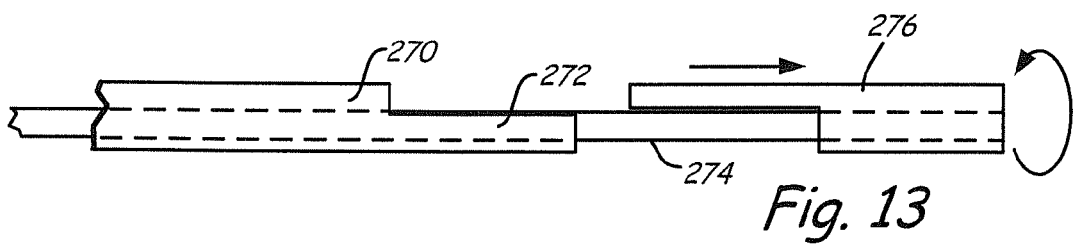
FIG. 13 is a side view of the torque coupler of FIG. 12 in which the torque coupler elements are disengaged.

Another embodiment of a torque coupler is shown in FIGS. 12 and 13. Tube 270 has a first coupling element 272 at its distal end. Corewire 274 has a second coupling element 276 at its distal end. As depicted in FIG. 12, first coupling element 272 engages second coupling element 276 to rotationally couple tube 270 with corewire 274. As depicted in FIG. 13, corewire 274 is moved toward the right relative to tube 270 to disengage first coupling element 272 and second coupling element 276 such that tube 270 and corewire 274 are not rotationally coupled.

Figure 14:
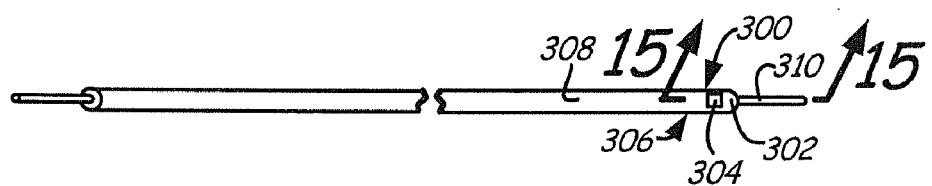
FIG. 14 is a side view of an integrated guiding device with a torque coupler based on electrostatic attraction.
Figure 15:
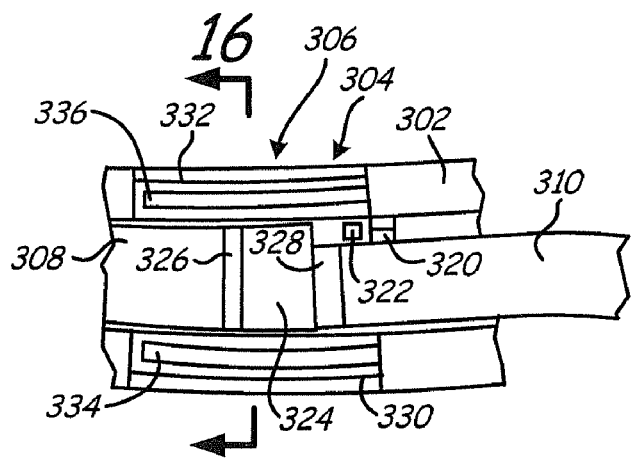
FIG. 15 is an expanded, sectional view of the torque coupler of FIG. 14 taken along line 15-15 of FIG. 14.

The torque coupling can also be controlled electromagnetically. A small battery can be placed near the distal end of the tube to power the coupling. Various electromagnetic couplings are possible to generate the torque coupling. An embodiment based on electrostatic attraction is shown in FIG. 14. Torque coupler 300 comprises a battery 302, a switch 304 and electrostatic coupler 306. Battery 302 is mounted on tube 308 and has a hole to provide for passage of corewire 310. Various designs of a switch can be used. Embodiments of switch 304 and electrostatic coupler 306 are shown in FIG. 15. In this embodiment, switch 304 is closed by pushing corewire 310 distal, i.e., toward the right in the orientation of FIG. 14, relative to tube 308, such that longitudinal movement of the corewire proximal relative to the tube is unobstructed by the switch and does not couple the torques. Switch 304 comprises a lead 320 connected to a first terminal of battery 302 and an optional spring 322 comprising a bend section of elastic metal.

Figure 16:
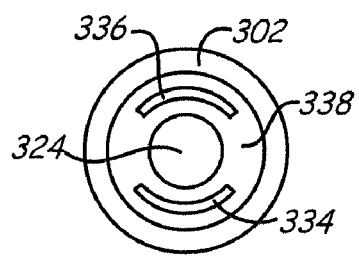
FIG. 16 is an expanded, sectional view of the torque coupler of FIG. 14 taken along line 16-16 of FIG. 15.
Figure 17:
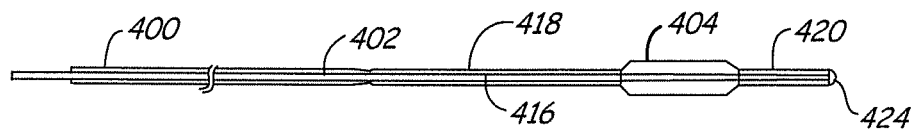
FIG. 17 is a sectional side view of a particular embodiment of an integrated embolism protection device and delivery tool.

Upon translating corewire 310 toward the right in the configuration of FIG. 15, corewire section 324 contacts lead 320 while deflecting spring 322. Corewire section 324 comprises an electrically conductive material, such as a metal and is surrounded by electrically insulating sections 326, 328. Electrostatic coupler 306 comprises deformable sections 330, 332 on tube 308 and electrically conductive sections 334, 336 that are connected to the opposite terminal of battery as lead 320. Electrically insulating material 338, such as an electrically insulating polymer, surrounds sections 334, 336 to prevent shorting of the battery due to contact between sections 334, 336 and corewire section 324. The sectional view of electrostatic coupler is depicted in FIG. 16. When the switch is closed, sections 334, 336 and corewire section 324 charge with opposite charges, like a capacitor such that deformable sections 330, 332 deflect to grip corewire 310 due to electrostatic attraction. Spring 322 can be used to open the switch when the corewire is not being pushed to close the switch.

The longitudinal freedom of motion of the tube with respect to the corewire provides for communication between the proximal and distal ends of the devices. Thus, the relative motion of the components can be used to actuate functional structures built into the distal end of the combined device. Functional medical components, such as actuatable medical treatment structures, are described in the following.

Functional Medical Components for Use With Integrated Guiding Device

In general, a functional medical component can be combined with an integrated guiding device. This can be particularly useful for an actuatable medical structure that can be actuated through the relative longitudinal motion of the corewire and the tube. Generally, this actuatable structure is located at or near the distal end of the integrated guiding device with corresponding actuation at the distal end of the device. For example, small grippers or fastener applicators can be placed at the end of the device. Suitable designs for a gripper and/or a fastener applicator that can be actuated with the relative motion of the corewire and the tube are described, for example, in U.S. Pat. No. 6,165,183 to Kuehn et al., entitled "Mitral And Tricuspid Valve Repair," incorporated herein by reference.

In addition, the functional medical component can be an embolism protection structure. Embolism protection structures of particular interest include, for example, fiber based embolism protection structures. As noted above, fibers with surface capillary fibers can be effectively used in embolism protection devices. In some embodiments, an embolism protection structure is placed at the distal end of the integrated guiding device. Relative motion of the corewire and the tube can be used to deploy the embolism protection structure from a confined narrow profile configuration for delivery to a deployed configuration at which the embolism protection structure is expanded within the vessel. The actuation, which is generated by the longitudinal motion of the tube relative to the corewire, can release the embolism protection structure from a constrained environments, as described further in U.S. patent application Ser. No. 10/414,909 to Ogle, entitled "Embolism Protection Device," incorporated herein by reference, or can directly drive a reconfiguration of the device into a form that filters the lumen of the vessel, as described further in U.S. Provisional Patent Application Ser. No. 60/489,044 to Ogle et al., entitled "Embolism Protection System," incorporated herein by reference.

Figure 18:
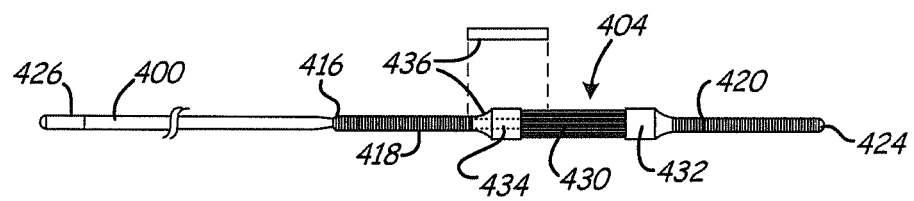
FIG. 18 is a side view of the integrated device of FIG. 17.
Figure 19:
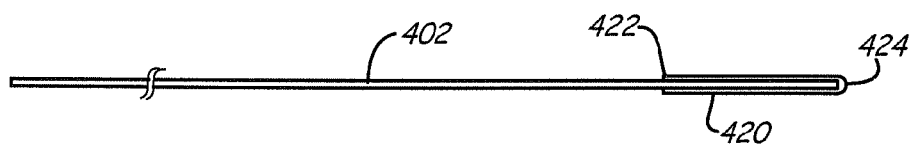
FIG. 19 is a side view of the corewire of the integrated device of FIG. 17.

One specific embodiment is shown in FIGS. 17-20. In this embodiment, the integrated guiding device comprises a tube 400, a corewire 402, and an embolism protection structure 404. Referring to the sectional view in FIG. 17 and the side view in FIG. 18, tube 400 has a tapered section 416 at its distal end that mimics the taper on a conventional corewire. A wire coil 418 is located over the tapered section 416. Corewire 402 is covered with a coil 420 at its distal end, as shown in FIG. 19. Coil 420 is connected with solder 422 and a weld 424, although other attachment approaches can be used. Tube 400, corewire 402, wire coil 418, coil 420 and grip 426 can all be formed from stainless steel, although other suitable materials can be used.

Figure 20:
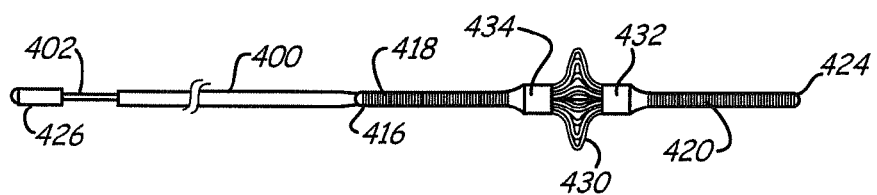
FIG. 20 is a side view of the device of FIG. 17 following expansion of the embolism protection device.

In this embodiment, embolism protection device 404 comprises a bundle of SCF fibers 430 attached at first attachment 432 and second attachment 434, as shown in FIGS. 18 and 20. A 0.1 inch long tube 436, which can be formed from polyimide polymer, is located within the second attachment 434 with corewire 402 extending within the tube. The fibers are swaged/crimped at the two attachments 432, 434 to a diameter of 0.033 inches with radio-opaque bands. After crimping, the fiber bundles are bonded at each end with an adhesive, such as cyanoacrylate.

The number of fibers in the bundle generally depends on the desired degree of filtration as well as the thickness of the fibers. In general, the number of fibers can be range from at least 10 fibers, in further embodiments from 25 fibers to 1,000,000 fibers, in other embodiments from 50 fibers to 10,000 fibers and in additional embodiments, from 100 fibers to 5,000 fibers. The length of the fibers can be selected based on the size of the corresponding vessel. When deployed, the centers of the fibers are projected across the lumen of the vessel. Thus, the unconstrained length of the fibers between attachment structures 432, 434 should be at least double the radius of the vessel. In some embodiments relating to the use of a plurality of fibers to expand within the lumen of a patient's vessel, it is generally appropriate to use fibers that have a length from about 2.2 to about 10 times the vessel radius, in some embodiments from about 2.4 to about 5 times the vessel radius and in further embodiments from about 2.6 to about 4 times the vessel radius. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure.

As used herein, SCF fibers refer broadly to fibers having channels or capillaries along the surface running generally along the length of the fiber or a portion thereof. Fibers have their usual meaning as structures with a length that is significantly larger than the dimensions along a cross section perpendicular to the length. The capillaries can run along substantially the entire length or a fraction thereof. Due to the presence of the capillaries, a cross section through the fiber at the capillary(ies) has a shape with an edge having changing curvatures.

SCF fibers for use in the medical devices are generally formed from biocompatible polymers. SCF fibers can be fabricated from synthetic polymers as well as purified biological polymers and combinations thereof. Suitable synthetic polymers include, for example, polyamides (e.g., nylon), polyesters (e.g., polyethylene teraphthalate), polyacetals/polyketals, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

Bioresorbable synthetic polymers can also be used such as dextran, hydroxyethyl starch, derivatives of gelatin, polyvinylpyrrolidone, polyvinyl alcohol, poly[N-(2-hydroxypropyl)methacrylamide], poly(hydroxy acids), poly(epsilon-caprolactone), polylactic acid, polyglycolic acid, poly(dimethyl glycolic acid), poly(hydroxy butyrate), and similar copolymers. Based on experience in the medical field, suitable resorbable polymers include, in particulaar, polylactic acid, polyglycolic acid, and copolymers and mixtures thereof.

Appropriate polymers also include biological polymers. Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers generally are bioresorbable. Purified biological polymers can be appropriately formed into a polymer material for further processing into fibers.

The properties of the surface channels and the corresponding cross-section of the fiber generally depends on the process used to form the fibers. U.S. Pat. No. 4,842,792 to Bagrodia et al., entitled "Drafting Process For Preparing A Modified Polyester Fiber," incorporated herein by reference, describes one approach for forming a fiber with a continuous surface "groove" that runs along the length of the fiber. The process in the '792 patent forms the groove starting from a conventional fiber. Another form of shaped fibers is described in U.S. Pat. No. 5,277,976 to Hogle et al., entitled "Oriented Profile Fibers," incorporated herein by reference. Other shaped fibers notches or channels are described in U.S. Pat. No. 5,458,963 to Meirowitz et al., entitled "Nonwoven Web Containing Shaped Fibers," incorporated herein by reference. Fiber with fairly complex surface channel geometry are described in U.S. Pat. No. 5,972,505 to Phillips et al., entitled "Fibers Capable Of Spontaneously Transporting Fluids," incorporated herein by reference. A further approach for forming a fiber with surface capillaries is described in U.S. Pat. No. 5,200,248 to Thompson et al. (hereinafter the '248 patent), entitled "Open Capillary Channel Structures, Improved Process For Making Capillary Channel Structures, And Extrusion Die For Use Therein," incorporated herein by reference. The Background section of the '248 patent additionally references a variety of alternative embodiments of approaches for forming fibers with surface channels or capillaries. Any of these approaches can be used. However, the fibers formed by the process of the '248 patent itself have desirable characteristics and versatility.

As with the fiber length, the thickness of the fibers can be selected appropriately for the particular use of the fiber. Fiber thickness can be measures in several ways. As described in the previous paragraph, the radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude. Also, in the fiber field, a pragmatic way has been developed to characterize fiber thickness without the need to resort to magnification of the fibers. Thus, fiber thickness can be measured in units of denier. Deniers correspond to the number of grams per 9,000 meters of yarn with a larger value corresponding to a thicker fiber. In some embodiments, suitable fibers have diameters from 50 microns to about 5 millimeter, in further embodiments from about 100 microns to about 2 millimeters, and in additional embodiments from about 150 microns to about 1 millimeter. As measured in denier, SCF fibers can have sizes ranging from about 0.1 denier to about 1000 denier in size, in additional embodiments from about 0.5 denier to about 250 denier, in some embodiments from about 1.0 denier to about 200 denier, in other embodiments from about 2.0 denier to about 100 denier and in further embodiments from about 3.0 denier to about 50 denier. A person of ordinary skill in the art will recognize that additional ranges of fiber thickness in diameter measurements or in denier are contemplated and are within the present disclosure. In one specific embodiment, the device comprises 480 of 6 denier SCF fibers in a bundle and a crossing profile of 0.033 inches (2.5 French).

Further characterization of the fibers can barrow from the approaches outlined in the '248 patent. In particular, the overall capillary sizes can be characterized. In some embodiments of interest, the fibers have a specific capillary volume of at least about 0.5 cc/g, in other embodiments at least about 1.0 cc/g, in further embodiments at least about 2.0 cc/g and in additional embodiments at least about 3.0 cc/g. Also, the specific capillary surface area can be at least about 500 $cm^2/g$, in some embodiments at least about 1000 $cm^2/g$, in further embodiments at least about 2000 $cm^2/g$, and in other embodiments at least about 3000 $cm^2/g$. A person of ordinary skill in the art will recognize that additional ranges of capillary volumes and capillary surface areas are contemplated and are within the present disclosure. Test methods for evaluating the specific capillary volume, the specific surface capillary area and the adhesion tension are described in detail in the '248 patent, which is incorporated herein by reference for the explicit description of the determination of these values.

It has been discovered that particular preparation processes for the fibers can lead to significantly improved uniformity of the performance of the embolism protection device. In particular, the fibers are twisted within the fiber bundle. In some embodiments, heat is also applied to the fibers. While any degree of twist can be desirable, twist can be applied to the fiber bundle of at least about 5 degrees and in further embodiments from about 180 degrees to about 360 degrees. Furthermore, multiple rotations, for example, about 360 degrees to about 1080 degrees, can further act to increase the density of fibers and may be advantageous. A person of ordinary skill in the art will recognize that additional ranges of twist within the specific ranges above are contemplated and are within the present disclosure. The twist can be applied by fastening one end of the fiber bundle, applying the twist and fastening the other end of the fiber bundle. A suitable torque coupler can facilitate the application of the twist to the fibers since the corewire does not rotate due to tension in the SCF fibers. This is described more specifically below with respect to a specific embodiment. With the application of a suitable twist, the embolism protection device is observed to perform with essentially uniform performance. Without the application of the twist, some of the fiber devices are observed to have small gaps in the filtering of the flow upon deployment. Thus, the twist provides for a commercial device with reproducible performance expected for medical devices in practice.

Specific Embodiments With a Fiber-Based Embolism Protection Structure Within an Integrated Guiding Device To summarize how various features can work together within an integrated guiding device, two specific embodiments of an integrated guiding device comprising an embolism protection structure is described in some detail. These devices are based upon the embolism protection structure similar to the structure in FIGS. 17-20 with specific features of the torque coupler specified. Referring to FIG. 21, integrated guiding device 450 comprises hypotube 452, corewire 454, torque coupler 456, embolism protection device 458, proximal coil 460, and distal coil 462. Torque coupled 456 comprises corresponding structural features in hypotube 452 and corewire 454 that interface to form the torque coupler. This embodiment is dimensioned to reach coronary arteries from a vein in the patient's thigh using conventional catheter procedures. In general, the device can be inserted through an incision in, for example, a patient's thigh, arm or neck. In general, the integrated guide device can be placed at various desired locations within a patient's arterial vasculature.

Referring to FIGS. 22A and 22B, hypotube 452 comprises notch 470 that forms a portion of the torque coupler 456. Apart from notch 470, hypotube 452 is a stainless steel tube with a constant inner diameter (0.0085±0.001 inches) and outer diameter of 0.014 inches. In this embodiment, hypotube 452 has a length of 60.5 inches. Stainless steel is convenient due to cost, biocompatibility and mechanical properties, but other materials and other dimensions can be used, as described above. Referring to FIG. 23, 1 inch at the distal end 472 of hypotube 452 is machined down to an outer diameter of 0.0125 inches with an approximately linear taper 474 over 0.25 inches between the 0.014 inch and the 0.0125 inch outer diameters. Proximal coil 460 is welded or otherwise bonded to the distal end 472 of hypotube 452, as shown in FIG. 23. Proximal coil 460 has an outer diameter of about 0.0125 inches and an inner diameter of about 0.009 inches.

Referring to FIG. 21, corewire 454 comprises a pull 480 fastened with a solder ball 482 at its proximal end. Corewire 454 also comprises a solder ball 484 at its distal end to maintain distal coil 462 on the corewire. The corewire is a stainless steel wire with a diameter of 0.0085 inches. Corewire 454 is coated with polytetrafluoroethylene to a maximum diameter of 0.0087 inches except for the distal about 2 inches, which is uncoated. Referring to FIGS. 22A, 22B, 24 and 25, corewire 454 has a flattened key portion 486 that forms a portion of torque coupler 456. Key portion 486 has a length of about 1 inch along the wire with a distal edge about 13.75 inches from the distal end of corewire 454. Referring to FIGS. 24 and 25, distal end 490 of corewire 454 is tapered over a distance of 1.485 inches. The distal 0.47 inches tapered distal end 490 is stamped to flatten the tip 492 in the same plane as the flattened key portion 486, as shown in the side views of FIGS. 24 and 25. Flattened tip has a width of 0.0075 inches and a thickness of about 0.0016 inches. Distal coil 462 fits over about the distal 1 inch of corewire 454. Corewire 454 has attachment elements 494, 496, 498 to facilitate attachment of distal coil 462 and filter structure 458.

Figure 26:
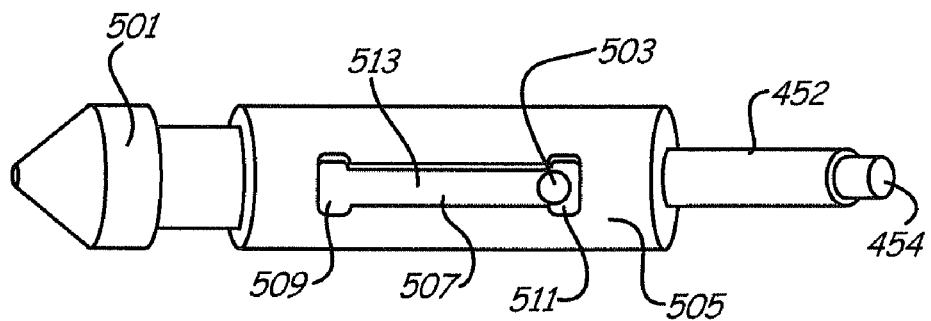
FIG. 26 is a fragmentary, side perspective view of the device of FIG. 21 with an alternative actuating tool.

An alternative embodiment of the pull element is shown in FIG. 26. Collet 501 is attached at the end of corewire 454, and push button 503 is placed near collet 501. A sliding collet 505 is fastened to hypotube 452. Sliding collet 505 has a slot 507 extending through its wall with enlarged openings 509, 511 at the ends of a linear section 513. Button 503 is depressed when aligned with linear section 513, but button 503 can extend outward at enlarged openings 509, 511 relative to its depressed configuration when aligned with linear section 513. Thus, the interface of sliding collet 505 with button 503 provides for two locked positions with a sliding motion between them. Sliding collet 505 and push button 503 function together as an actuation element for the embolism protection device through the control of the movement of corewire 454 with respect to hypotube 452. When button is in bulge 511, the embolism protection device is locked in a low profile delivery/recovery configuration. When button is in enlarged opening 509, the embolism protection device is locked in its deployed configuration.

Notch 470 fits within flattened key portion 486 to form torque coupler 456. Torque coupler 456 is shown in detail in FIGS. 22A-22C. Once torque coupler 456 is fully formed, the longitudinal motion of corewire 454 is limited within hypotube 452 such that sufficient movement of corewire 454 relative to hypotube 452 to control embolism protection device 458 while limiting complications due to unwanted movement of corewire 454. However, the relative motion of corewire 454 with respect to hypotube 452 can also be limited by an actuating tool or other structure at the proximal end of the elements. The formation of torque coupler 456 is described further below. To form the key portion along the corewire, the corewire is placed within a block fixture 500, shown in FIGS. 27, 28 and 29. Block fixture 500 has a partial circular channel 502. When placed within channel 502, a portion of the corewire extends above the surface of the block. By grinding the wire to the surface of block fixture 500, the flattened key is formed in corewire 454. Block fixture 500 can be formed from stainless steel.

Embolism protection structure 458 connects between corewire 454, proximal coil 460 and distal coil 462. Referring to FIG. 30, a marker band 498 abuts the distal end of proximal coil 460, about 1.6 inches from the distal end of corewire 454. Marker band 498 can be formed from a radio opaque material such that it can be viewed using x-rays for determining position within the patient's body. Suitable radio-opaque materials include, for example, radio-opaque polymers. Radio-opaque polymers include, for example, iodinated and brominated polymers, as described in U.S. Pat. No. 6,475,477 to Kohn et al., entitled "Radio-Opaque Polymer Biomaterials," incorporated herein by reference. Marker band 498 is attached near the proximal end of the filter cartridge structure 458. Embolism protection structure 458 comprises a fiber bundle 510 bound with bands 512, 514. At its proximal end, the fiber bundle is bound over a polymer tube 516 that rides over corewire 454. Adhesive 518 binds fiber bundle 510 to polymer tube 516, marker band 498 and proximal coil 460 at its proximal end, and to corewire 454 and distal coil 462 at its distal end.

To form the device, a filter cartridge comprising fiber bundle 510, bands 512, 514 and tube 516 is fed over corewire 454 and the corewire is fed through hypotube 452. The distance from the distal end of corewire 454 is measured to locate the flat grind of the corewire within hypotube 452. Hypotube 452 is placed within a fixture designed to control the amount of crimp. The parts are aligned longitudinally based on marking on corewire 454. Hypotube 452 is crimped to corewire 454 to form torque coupler 458. The tube and corewire are then longitudinally locked with limited longitudinal motion provided. The distal end of the filter cartridge is then fastened with adhesive to corewire 454. The fiber cartridge is twisted and the proximal end of the fiber cartridge is bonded with adhesive to proximal coil 460. The torque coupling of the corewire to the hypotube and proximal coil prevent rotation that would undo the twist in the fiber cartridge.

The second specific embodiment of the integrated guiding device is the same as the embodiment in FIGS. 21-30 except for the torque coupling feature of the corewire and for the actuation element. Specifically, the design of the sliding collet and the corewire result in the rotation of the corewire relative to the hypotube while the embolism protection device is deployed. This rotation of the fiber-based embolism protection device provides for even more consistent deployment of the fibers across the vessel.

Referring to FIG. 31, corewire 520 has the same structure as corewire 454 except that flattened key portion 486 is replaced with deployment guide 522. Deployment guide 522 comprises a thin section 524 and a key section 526. Sectional views of thin section 524 and key section 526 are shown in FIGS. 32 and 33, respectively. Thin section 524 has a diameter that is smaller than adjacent section of corewire 520 such that thin section 524 avoids contacting notch 470 of hypotube 452 when they are positioned at a common longitudinal position. Key section 526 has a similar cross sectional structure as flattened key portion 486. Key section 526 provides for torque coupling while thin portion 524 provides for rotation of the corewire 520 relative to hypotube 452 of FIG. 21. Thin section 524 and key section 526 can be formed, for example, analogously to flattened key portion 486, as described above.

Figure 34:
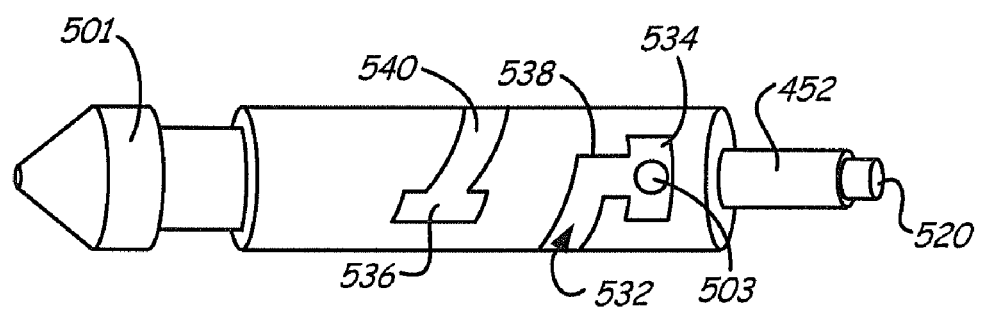
FIG. 34 is a fragmentary, side perspective view of a second alternative acutating tool for use with the corewire of FIG. 31.

Referring to FIG. 34, rotating collet 530 replaces sliding collet 505 for interfacing with the embodiment of corewire 520 in FIG. 31. Rotating collet 530 similarly is attached to hypotube 452. Rotating collet 530 has a rotating slide 532 extending through the walls of the collet. Rotating slide 532 has a first enlarged opening 534, a second enlarged opening 536, linear slide section 538 and a corkscrew slide section 540. Push button 503 is depressed when aligned with linear slide section 538 or corkscrew slide section 540. Push button 503 extends outward when aligned with enlarged opening 534 or enlarged opening 536 relative to its position when aligned with slide sections 538, 540. Thus, corewire 520 is locked relative to hypotube 452 when pushbutton 503 is aligned with enlarged openings 534, 536. Corewire 520 can move relative to hypotube 452 when push button 503 is aligned with slide sections 538, 540.

For the placement of the embolism protection device, push button 503 is positoned in enlarged opening 534 with the embolism protection device locked in a low profile configuration. Once the device is positioned as desired within the patient for deployment of the device, push button 503 is depressed, and transit of the push button along linear slide 538 provides for notch 470 to disengage from key section 526. As push button 503 moves along corkscrew slide section 540, corewire 520 is rotated relative to hypotube 452. Since notch 470 is then positioned at thin section 524, the rotation of hypotube 452 relative to corewire 520 can be transmitted to their distal end to rotate the fibers of an embolism protection device while it is being deployed. When pushbutton 503 reaches extended opening 536, the push button projects into extended opening 536, and the embolism protection device is locked in its deployed position. This process can be reversed to put the embolism protection device into a recovery configuration.

Distribution and Packaging

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition. The components can be packaged individually or together.

Various devices described herein can be packaged together in a kit for convenience. The kit can further include, for example, labeling with instruction for use and/or warnings, such as information specified for inclusion by the Food and Drug administration. Such labeling can be on the outside of the package and/or on separate paper within the package.

The embodiments above are intended to be illustrative and not limiting. Additional embodiments are within the inventive concepts. Although the present invention has been described with reference to particular embodiments, workers skilled in the art will recognize that changes may be made in form and detail without departing from the spirit and scope of the invention.

What we claim is:

1. An embolism protection device comprising a tube with a lumen, a corewire that extends from the distal end to the proximal end of the tube through the lumen of the tube, and a bundle of at least 50 fibers having a first end and a second end,
   wherein the first end of the fibers are collectively attached to move with the tube, the second end of the fibers are collectively attached to move with the corewire at a location distal to the distal end of the tube,
   wherein the device has a first narrow profile configuration with a bundle of fibers being generally aligned and the respective ends of the fiber bundle being generally twisted relative to each other about an axis aligned along the corewire,
   wherein the device has an extended second configuration with the unattached portion of the fibers flare outward with respect to the first narrow profile configuration to form a three dimensional porous filtration matrix to fill the lumen of a vessel,
   wherein the transition between the first and second configurations of the device are achieved through longitudinal movement of the corewire relative to the tube, and wherein the device has structure that limits the longitudinal motion of the corewire relative to the tube.

2. The embolism protection device of claim 1 wherein the fibers comprise polymeric surface capillary fibers.

3. The embolism protection device of claim 2 wherein the surface capillary fibers comprise polyester.

4. The embolism protection device of claim 1 further comprising a fiber support wherein the fiber support comprises an adhesive that secures the fibers.

5. The embolism protection device of claim 1 further comprising a fiber support that comprises a first element attached to the first end of the fibers and a second element attached to the second end of the fibers.

6. The embolism protection device of claim 5 wherein the first element of the fiber support is in a spaced apart relationship from the second element of the fiber support in the first configuration and the second configuration has the first element and the second element of the fiber support in closer proximity relative to each other.

7. The embolism protection device of claim 6 wherein the first element is generally cylindrical with a central passage and wherein the corewire passes through the central passage and is attached to the second element.

8. The embolism protection device of claim 5 wherein the fiber support structure comprises a radio-opaque element.

9. The embolism protection device of claim 1 further comprising a torque coupler that can couple the rotational motion of the tube with the rotational motion of the corewire.

10. The embolism protection device of claim 9 wherein the torque coupler is engaged at some longitudinal positions of the corewire and the tube.

11. The embolism protection device of claim 10 further comprising an actuation element that automatically rotates the corewire relative to the tube over a portion of the longitudinal motion of the corewire relative to the tube.

12. The embolism protection device of claim 5 wherein the fiber support structure comprises a metal band that encircles a bundle of fibers near the fiber ends to secure the fibers.

13. The embolism protection device of claim 1 wherein the device in the first configuration can pass through a catheter with an appropriate size to enter a human vessel.

14. The embolism protection device of claim 1 wherein the fibers have a length from about 1 mm to about 25 mm.

15. The embolism protection device of claim 1 wherein the device comprises from about 50 to about 5000 fibers.

16. The embolism protection device of claim 1 wherein the device comprises fibers with a size from about 0.5 denier to about 25 denier.

17. The embolism protection device of claim 1 wherein the fibers comprise surface capillary fibers with a specific capillary volume of at least about 0.5 cc/g.

18. The embolism protection device of claim 1 wherein the first end of the fibers is twisted by at least about 5 degrees relative to the second end of the fibers.

19. The embolism protection device of claim 1 wherein the ends of the fiber bundle are twisted in a configuration in which the fibers are flared in an extended configuration.

20. The embolism protection device of claim 1 wherein the porous filtration matrix allows the passage of a substantial majority of particulates that have a diameter less than 0.01 mm and traps emboli having a size larger than about 50 microns.

* * * * *

UNITED STATES PATENT AND TRADEMARK OFFICE
CERTIFICATE OF CORRECTION

| | | |
|---|---|---|
| PATENT NO. | : 7,988,705 B2 | |
| APPLICATION NO. | : 10/979439 | |
| DATED | : August 2, 2011 | |
| INVENTOR(S) | : Jason A. Galdonik et al. | |

It is certified that error appears in the above-identified patent and that said Letters Patent is hereby corrected as shown below:

Column 20, line 56, "with a bundle" should be changed to --with the bundle--

Signed and Sealed this
Fifteenth Day of November, 2011

David J. Kappos
*Director of the United States Patent and Trademark Office*